US009561399B2

(12) United States Patent
Acosta et al.

(10) Patent No.: US 9,561,399 B2
(45) Date of Patent: Feb. 7, 2017

(54) LUNG INSTRUMENT TRAINING DEVICE AND METHOD

(71) Applicants: Frank Acosta, Miami, FL (US);
William Rose, Miami, FL (US)

(72) Inventors: Frank Acosta, Miami, FL (US);
William Rose, Miami, FL (US)

(73) Assignee: Lung Trainers, LLC, Miami, FL (US)

( * ) Notice: Subject to any disclaimer, the term of this patent is extended or adjusted under 35 U.S.C. 154(b) by 0 days.

(21) Appl. No.: 14/697,779

(22) Filed: Apr. 28, 2015

(65) Prior Publication Data

US 2016/0317865 A1    Nov. 3, 2016

(51) Int. Cl.
*A63B 23/18*    (2006.01)

(52) U.S. Cl.
CPC ..................... *A63B 23/18* (2013.01)

(58) Field of Classification Search
CPC ... A63B 23/18; A63B 21/008; A63B 21/0083; A63B 21/088; A63B 23/0244; A63B 23/032; A63B 23/185
See application file for complete search history.

(56) References Cited

U.S. PATENT DOCUMENTS

| | | | | |
|---|---|---|---|---|
| 4,171,804 A * | 10/1979 | Thead, Jr. | ............... | A63B 23/18 482/13 |
| 4,403,616 A * | 9/1983 | King | ............... | A63B 23/18 482/13 |
| 4,444,202 A * | 4/1984 | Rubin | ............... | A61B 5/0875 482/13 |
| 5,984,873 A * | 11/1999 | Crumb | ............... | A61B 5/0875 482/13 |
| 6,238,353 B1 * | 5/2001 | Weinstein | ............ | A61B 5/0875 600/538 |
| 6,723,024 B2 * | 4/2004 | Levine | ............... | A63B 23/185 482/13 |
| 2005/0165322 A1 * | 7/2005 | Bryant | ............... | A61B 5/0875 600/538 |
| 2008/0263829 A1 * | 10/2008 | Diasio | ............... | A01K 87/08 16/421 |
| 2014/0150801 A1 * | 6/2014 | Rusher | ............... | A63B 23/18 128/207.16 |

* cited by examiner

*Primary Examiner* — Loan H Thanh
*Assistant Examiner* — Megan Anderson
(74) *Attorney, Agent, or Firm* — Peter A. Koziol, Esq.; Assouline & Berlowe, P.A.

(57) ABSTRACT

A lung instrument training device including at least one weighted insert, a hollow cylinder having a bottom and a top, wherein the weighted insert is positioned within the hollow cylinder, and a tube, wherein the distal end of the tube is connected to the bottom of the hollow cylinder, and a user breathes into the proximal end of the tube. A method for exercising lung capacity, strength and control including exhaling air from a user's lung in a tube connected to a cylinder, moving at least one weighted insert positioned inside the cylinder; and regulating the position of the weighted inserts within the cylinder.

11 Claims, 5 Drawing Sheets

LUNG INSTRUMENT TRAINING DEVICE AND METHOD

CROSS-REFERENCE TO RELATED APPLICATIONS

N/A

FIELD OF THE INVENTION

The invention broadly relates to lung exercises, more specifically to a device to strengthen lungs and increase lung control and capacity, and even more particularly to a method to strengthen lungs and increase lung control and capacity.

BACKGROUND OF THE INVENTION

Wind instruments are musical instruments that include some type of resonator. A column of air is vibrated by a user blowing air into or over a mouthpiece located at the end of a resonator. The pitch of the vibration is determined by the length of the tube in conjunction with modifications of the effective length of the vibrating column of air. Common wind instruments include horns, trumpets, recorders, flutes, and saxophones.

Musicians playing wind instruments require high levels of lung capacity and lung and diaphragm control to hit the applicable notes and note lengths while playing a composition. Each wind instrument requires different levels of air regulation and exhaling. Plus, musical compositions vary in difficulty, thereby increasing the lung demand on the musician playing the instrument.

A musician must have the lung control and capacity to breath sufficient air into the instrument to properly play the musical notes and timing required in the musical composition. Although there are a myriad of exercise equipment to exercise a person's muscles or increase their cardiovascular stamina, there is a need to develop a device and method to increase a person's lung capacity.

A new student, without training, can only play certain wind instruments for a limited period of time before they run out of air, i.e. they become "winded." The more the student plays the instrument over time, his lung capacity increases due to the training. However, this takes a long time to occur as the training only occurs as the student practices with the instrument. The size of some wind instruments makes playing them difficult to play frequently. Also, some environments do not allow students to practice frequently due to the loud noise eminating from the wind instrument.

There are some devices in the market that develop air capacity for users. However, these devices do not have a system to train a user's lung by regulating weight suspended in air. Moreover, existing devices do not mimic musical instruments for training purposes.

As such, there is a need for a lung capacity training device and method that changes based on the user's needs. As the user learns to use an instrument or advances to a more complex instrument, the user needs to increase his lung capacity, strength and control. The training requires a calculated system to increase a user's lung capacity, strength and control based on current and future needs.

As can be derived from the variety of devices and methods directed at increasing lung capacity, many means have been contemplated to accomplish the desired end, i.e., training a user's lungs. Thus, there is a long-felt need for a device and method to aid a user in increasing their lung capacity, strength and control.

BRIEF SUMMARY OF THE INVENTION

The present invention broadly includes a at least one weighted insert, a hollow cylinder having a bottom and a top, where the weighted insert is positioned within the hollow cylinder. The present invention also includes a tube, where the distal end of the tube is connected to the bottom of the hollow cylinder and a user breathes into the proximal end of the tube.

In a further embodiment, the present invention includes a mouthpiece for a user to breath into that is connected to the proximal end of the tube.

In yet a further embodiment, the present invention includes an anti-bacterial coating on the inner surface of the breathing tube.

In an additional embodiment, the present invention includes a timer to track the time of engagement by a user exercising with the lung instrument training device.

It is a general object of the present invention to provide a method for exercising lung capacity by exhaling air from a user's lung in a tube connected to a cylinder, moving at least one weighted insert positioned inside the cylinder, and regulating the position of the weighted inserts within the cylinder.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. It should be appreciated that the term "breathing" is synonymous with terms such as "exhaling", "inhaling", "blowing", "gasping", "puffing", etc., and such terms may be used interchangeably as appearing in the specification and claims. Although any methods, devices or materials similar or equivalent to those described herein can be used in the practice or testing of the invention, the preferred methods, devices, and materials are now described.

Exercising a user's lungs improves a user's breathing capacity. As with swimming and marathon athletes, training improves oxygen intake and the cardiovascular system. The present invention is preferably used in the music industry. However, the lung instrument training device provides support in numerous fields, including but not limited to, athletics and medicine. The present invention also promotes greater lung control and strength.

Figure 1:
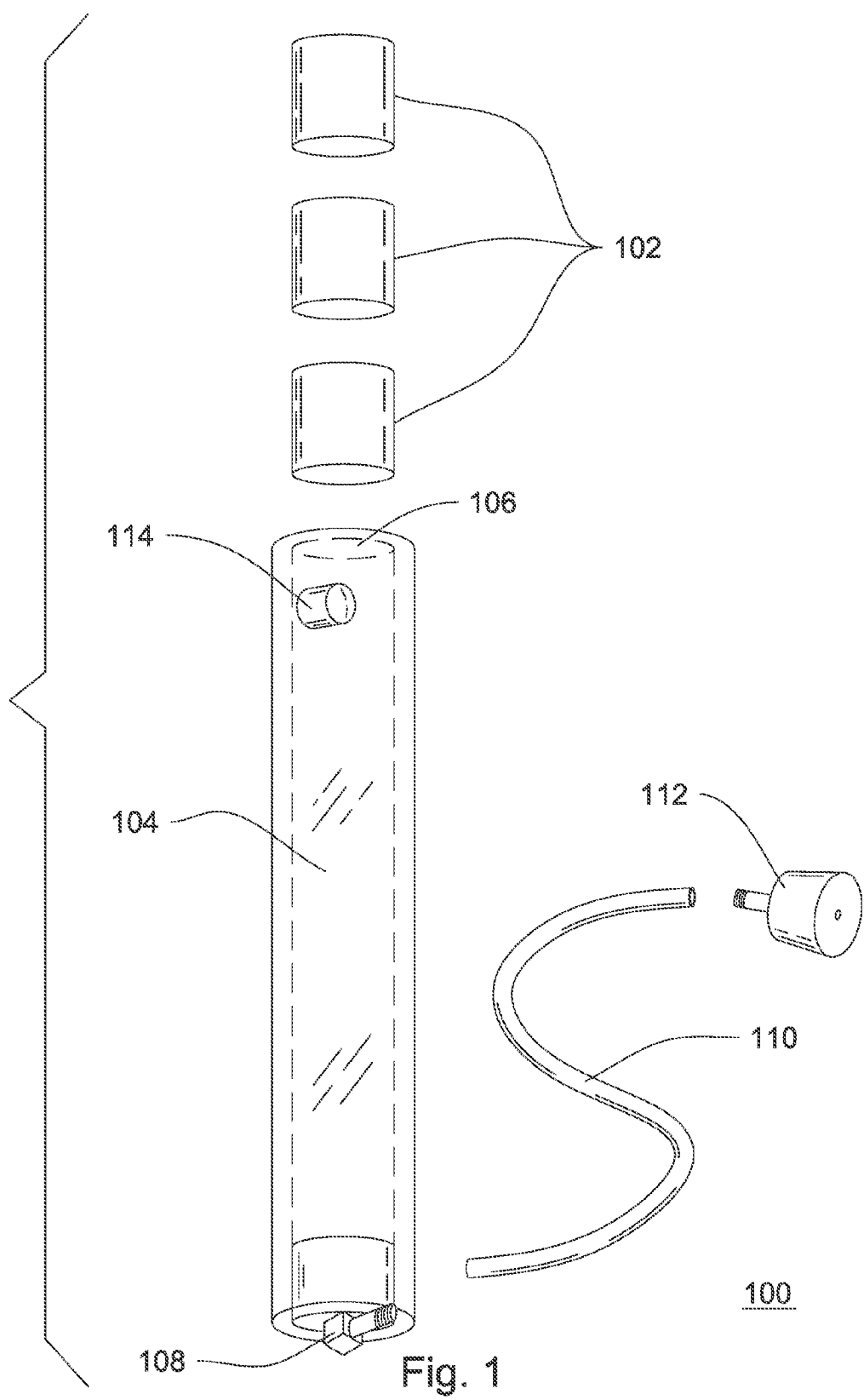
FIG. 1 is an exploded view of the lung instrument training device.
Figure 2:
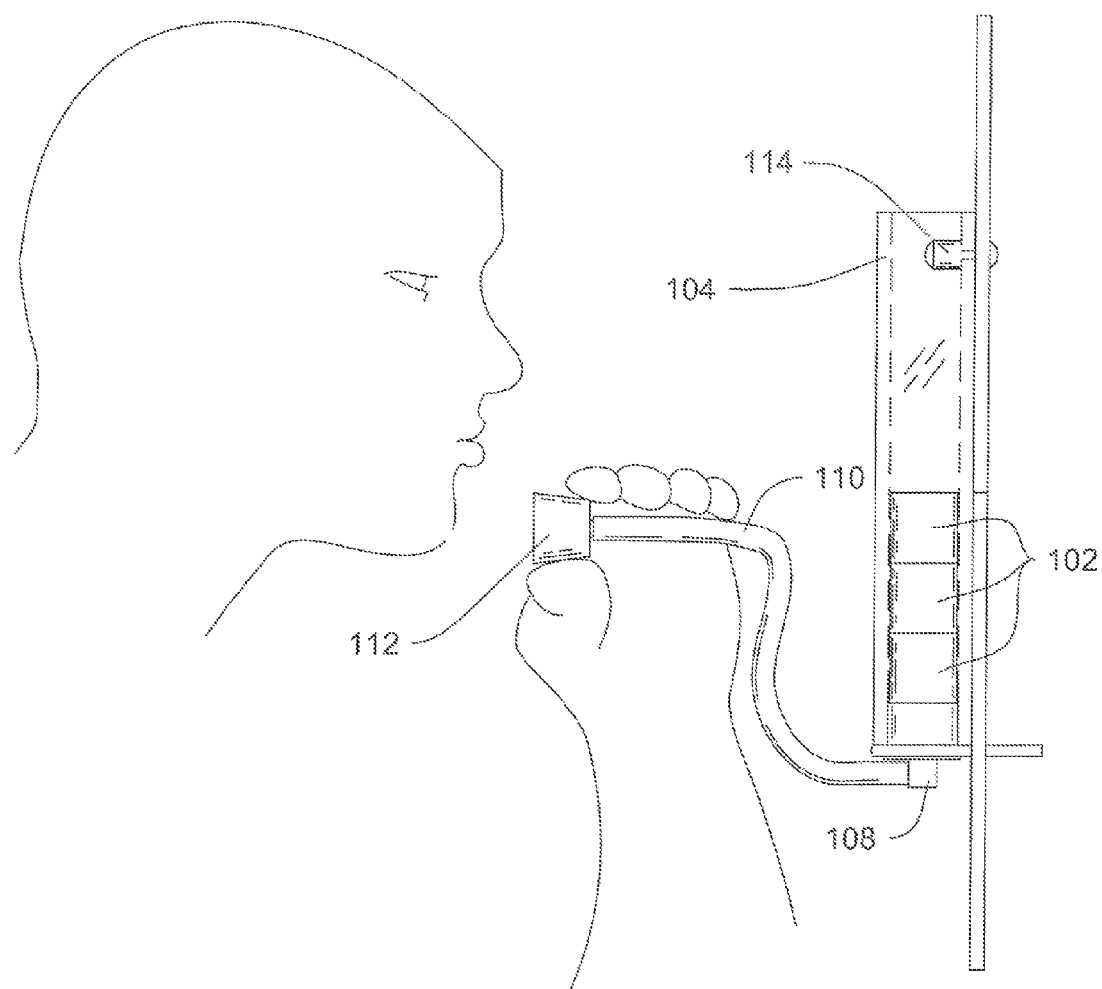
FIG. 2 is a front cut-out view of the weighted inserts inside the cylinder of the present invention.

Adverting now to the figures, FIGS. 1 and 2 illustrate a lung instrument training device 100 for a user to exercise their lungs. FIG. 1 illustrates three weighted inserts 102 enclosed within cylinder 104. Weighted inserts 102 are preferably made of non-oxidized material, such as copper or stainless steel. However, any material may be used for weighted inserts 102 in the present invention. Cylinder 104 is preferably made from plastic or acrylic. Preferably, the material is translucent so the user can view the inside chamber of cylinder 104.

Cylinder 104 has a hollow center in which weighted inserts 102 are inserted through cylinder opening 106 at the top of cylinder 104. As shown in FIG. 1, the bottom portion of cylinder 104 is enclosed. Tube connector 108, located underneath the enclosed bottom of cylinder 104, connects to the distal end of tube 110. Tube connector 108 is preferably a stainless steel L connector use to connect cylinder 104 to tube 110. The proximal end of tube 110 connects to mouthpiece 112.

To use the lung instrument training device 100, a user places mouthpiece 112 to his mouth. The user then exhales, or blows air, from his lungs into mouthpiece 112. Depending on the training program selected, a user chooses to take a deep breath prior to engaging mouthpiece 112 to his mouth. The air exhaled from the user's lungs enters mouthpiece 112, travels through tube 110, and enters tube connector 108.

The air then flows from tube connector 108 into cylinder 104, filling the internal chamber of cylinder 104 exerting pressure on weighted inserts 102. As the user increases the force of air exhaled into mouthpiece 112, the force exerted onto weighted inserts 102 increases. When the force of the air within cylinder 104 exceeds the weight of weighted inserts 102, the weighted inserts 102 move along the length of cylinder 104. If enough air is exhaled into mouthpiece 112, weighted inserts 102 travel through cylinder 104 and stop at weight stop 114. Weighted inserts 102 travel through cylinder 104 due to the radial gap between the weighted inserts 102 and cylinder 104.

As shown FIG. 2, cylinder 104 includes outer cylinder surface 202 and inner cylinder surface 204. The diameter of weighted inserts 102 is smaller than the inside diameter of inner cylinder surface 204. The distance between the diameter of weighted inserts 102 and the inner cylinder surface 202 is defined as air gap 206. The distance of air gap 206 correlates to the amount of force required by a user breathing into lung instrument training device 100. The greater the air gap 206, the greater the exhale force required by the user. Air gap 206 provides the spacing needed to allow weight inserts 102 to travel through cylinder 104 as air enters and fills cylinder 104.

The objective of the present invention is for a user to regulate the air being exhaled from his lungs, into mouthpiece 112, to suspend weighted inserts 102 within cylinder 104. The user regulates the exhaling of air from his mouth into lung instrument training device 100 to regulate the travel of weighted inserts 102 within cylinder 104.

Figure 3:
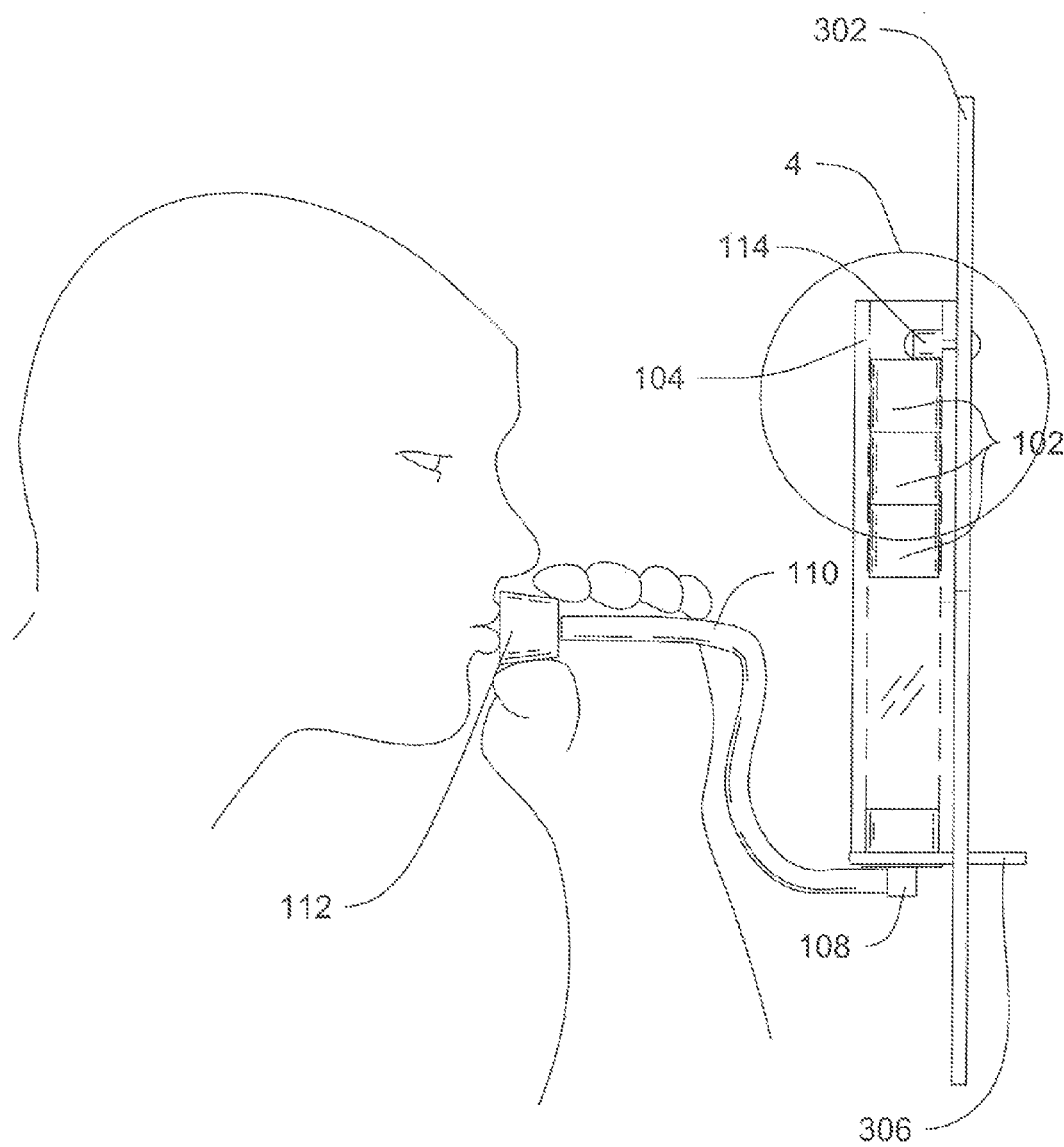
FIG. 3 is a side view of a user preparing to exhale into the present invention while the weighted inserts are at rest.

As shown in FIG. 3, weighted inserts 102 remain at the bottom of cylinder 104, enclosed within the interior of cylinder 104 when the device is disengaged. As the user exhales into lung instrument training device 100 with sufficient force, weighted inserts 102 travel within cylinder 104. Although the travel of weighted inserts preferably occurs in the vertical position, an alternative embodiment allows the user to optimally vary of the angle of operation of lung instrument training device 100.

Figure 4:
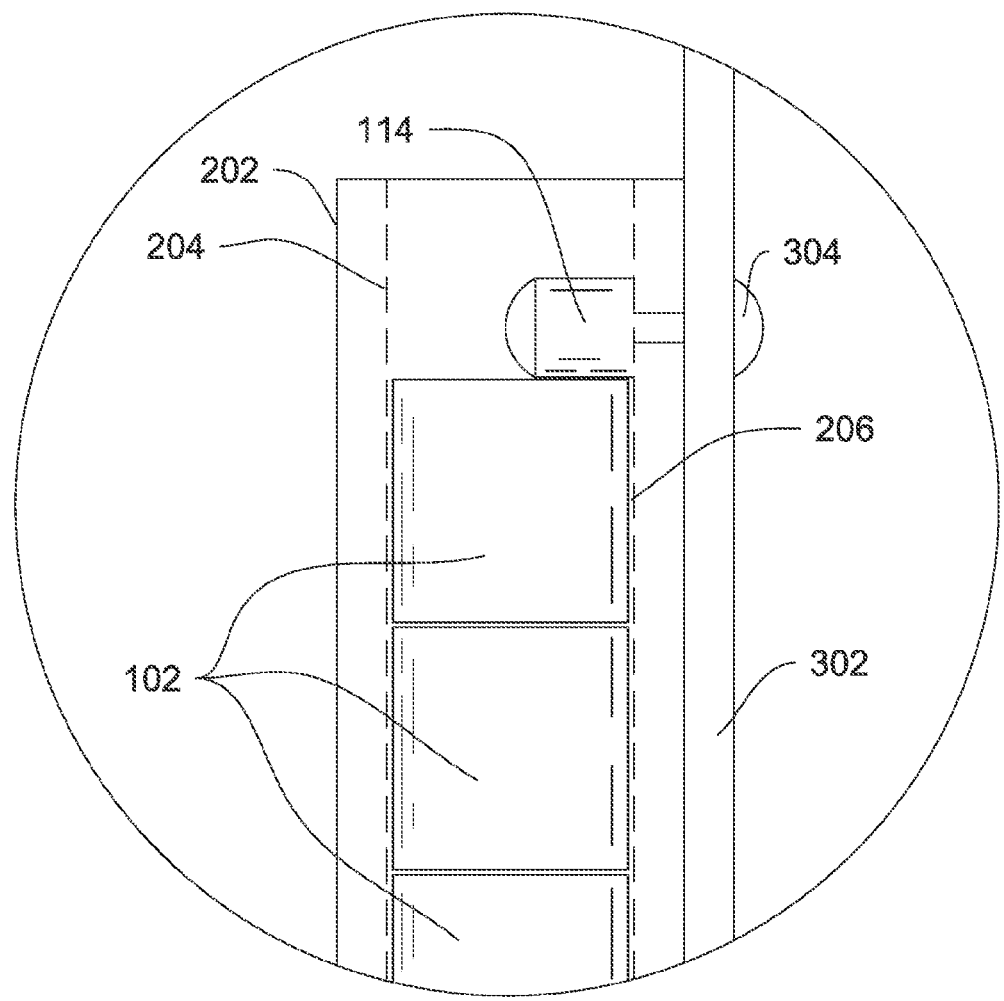
FIG. 4 is a side view of a user exhaling into the present invention while the weighted inserts are at the maximum travel position inside the cylinder.

When the user over-exhales into the present invention, the weighted inserts 102 travel to the top of cylinder 104 and hit stopper 116, depicted in FIG. 4. Once weighted inserts 102 hit stopper 116, increased air flow by the user is wasted as the weighted inserts 102 cannot travel past stopper 116 within cylinder 104. The benefit of the present invention is not achieved when the weighted inserts 102 remain at the bottom of cylinder 104 or hit stopper 116. The present invention is designed to train a user's lungs to increase lung capacity by regulating the amount of air a user exhales, i.e. breathes, into the device, to suspend weights inserts 102 within cylinder 104.

Figure 5:
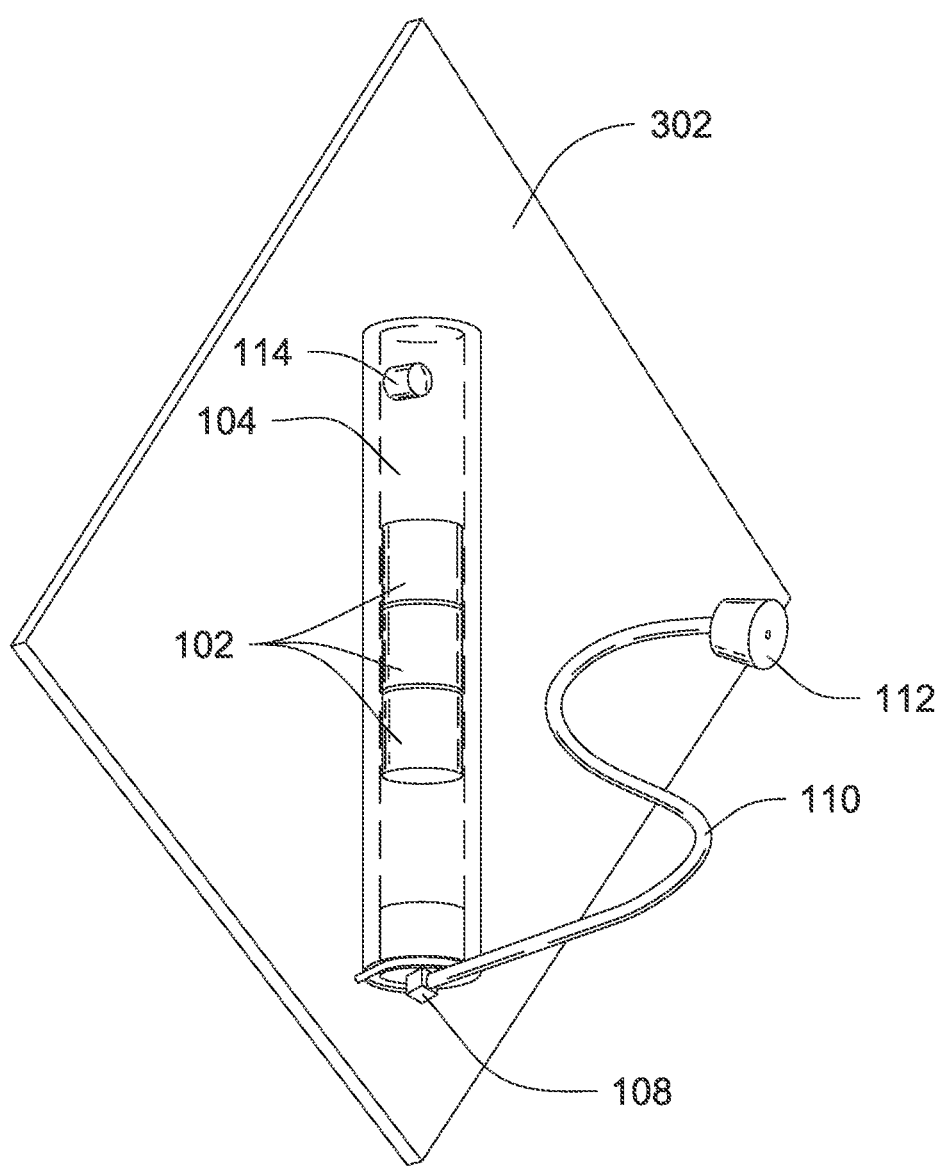
FIG. 5 is a perspective view of the present invention where the weighted inserts are suspended in air within the cylinder due to user regulation of air flow.

Regulation of the air the user breathes into mouthpiece 112 preferably keeps weighted inserts 102 suspended within cylinder 104. FIG. 5 illustrates a user regulating the air flow the user breathes into the present device to keep the weighted inserts 102 suspended within cylinder 104. The user increases the air flow output to move the weighted inserts 102 higher within the cylinder 104. Conversely, the user decreases the air flow output to move the weighted inserts 102 lower within the cylinder 104. In the context of the present invention, air flow output is the amount of air a user exhales from his lungs into the mouthpiece 112, tube 110, or other entry point of the present device.

One of the many uses of the present invention is to aid musicians that must exhale air from their lungs into a musical instrument, such as but not limited to a tuba, saxophone, and recorder. A new student learning a musical instrument needs to train his lungs to increase his lung capacity. This aids the student in playing complex musician compositions.

As with any type of training, practice is required. First, the user must establish a baseline. For example, a new student's lung capacity requires only one weighted insert 102 to properly regulate the weighted insert 102 in a suspended position within cylinder 104. As the student uses the present invention with one weighted insert 102, his lung capacity increases. This training is similar to muscle training to increase muscle strength for athletes and weightlifters.

For the student to increase lung capacity, a second weighted insert is added to the cylinder 104 of the present invention. The student then attempts to regulate the two weighted inserts 102 in a suspended position within cylinder 104. After practicing with the second weighted insert 102 added, the students' lung capacity increases. Additional weighted inserts 102 are added based on the specific needs of the user. The length of cylinder 104 varies based on the height and number of weighed inserts 102 used.

Maintaining the appropriate regulation of air flow output by the student into the input of the present invention exercises the user's lungs. The student who started with lung capacity to play a recorder, after training with the present invention, can now play a saxophone that requires more lung capacity and breathing regulation.

As with any training program, the number of weighted inserts 102 and the weight themselves are variable based on the needs of the user. Medical patients, such as those recovering from surgery or cancer treatments, will use the present invention to improve their lung capacity. The ability to adjust the number of weighted inserts and weight of the present invention provides a variable solution to improve a user's lung capacity, strength and control.

In an exemplary embodiment, mouthpiece 112 is connected to the proximal end of tube 110. Mouthpiece 112 provides a smooth fit to the user's mouth when exhaling air from his lungs into the present invention. Although mouthpiece 112 is made from numerous materials, the preferred composition of mouthpiece 112 is rubber. Alternatively, mouthpiece 112 is shaped to mimic the mouthpieces of various musical instruments to better assist musicians training to use a particular instrument.

In yet another exemplary embodiment, the weighted inserts are formed in the following shapes: cylinder, sphere, or cube. The present invention also includes a timer to keep track of the amount of time the user is actively regulating his air flow to keep weighted inserts 102 suspended. Moreover, instead of a timer, a metronome is used for musicians to train regulating the weighted inserts 102 in a suspended state. A musician will use the counts of the metronome to know how many musical counts they can keep the weighted inserts 102 in a suspended state. This provides a measurable date point of how long the musician can hold various musical notes.

In a group context, users of the present invention engage in competition to determine which user suspends weighted inserts 102 the longest by regulating the user's breathing into the mouthpiece 112. This use of the present invention promotes a competition that facilitates training the user's lung capacity. To maintain a sterile environment, mouthpiece 112 is disengaged with tube 110 and changed for each user using the present invention.

A variety of users benefit from increasing lung capacity, strength and control using the present invention. Cancer and other medical patients use the present invention to recover from traumatic injuries to their bodies. Instead of merely exhaling or inhaling with a high force to test lung capacity, the present invention regulates the user's breathing using training programs to increase lung capacity. Moreover, athletes, such as swimmers and long distance runners, use the present invention to increase their lung capacity, strength and control for taxing athletic events.

Another exemplary embodiment includes attaching the cylinder 104 of the present invention to mounting plate 302, as shown in FIGS. 3, 4, and 5. A user holds the present invention substantially vertically in use. However, to use the present invention more effectively, cylinder 104 is secured to mounting plate 302 using top connector 304 and bottom connector 306. Mounting plate 302 is optionally fastened to a wall in optimal position for the user to breath into the present invention and view the weighted inserts 102. In another embodiment, mounting plate 302 is part of a carrying case that, when opened, turns into a stand. This allows a user to carry the present invention with them and use it a variety of environments without directly attaching the present invention to a wall, door, or other surface.

Bottom connection 306 is a U shaped fastening device with bolts that connect the cylinder 104 to the mounting plate 302. Similarly, top connection 304 is a screw that travels through mounting plate 302 and cylinder 104. A nylon or silicone sleeve located within cylinder 104 secures the screw, thereby connecting mounting plate 302 to cylinder 104. The use of a nylon or silicone sleeve provides a stopping point for the weighted inserts 102, similar to stopper 116.

In another exemplary embodiment, the inner surface of tube 110, and corresponding connections, are lined with an anti-bacterial coating. Silver is a preferred anti-bacterial coating. During prolonged use, the air passing through tube 110 includes saliva and bacteria from the user's mouth. These substances, when left to sit over time, breed bacteria that will cause disease or sickness to the user. Use of an anti-bacterial coating maintains a sterile environment for use by multiple users.

The present invention also includes a method for improving lung capacity. A user selects the number of weighted inserts 102 to begin using the present invention and places them in cylinder 104. The user places his mouth onto a mouthpiece 112 of the lung instrument training device 100. The user exhales, expressing air from his lungs into mouthpiece 112, through tube 110 and tube connection 108, and into cylinder 104. Next, the force of the exhaled air from the user moves the weighted inserts 102 that are located inside of cylinder 104. The user then regulates his air flow into the mouthpiece 112 to keep inserted weights 102 suspended within cylinder 104. Once the user is unable to continue regulating his air flow, the user disengages his mouth from mouthpiece 112, thereby causing weighted inserts 102 to rest at the bottom of cylinder 104.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

We claim:
1. A lung instrument training device, comprising:
   more than one weight adjusting inserts wherein said weight adjusting inserts are selected to change the overall weight a user exercises against;
   a hollow chamber having a bottom and a top, wherein one or more of said weight adjusting inserts are positioned within said hollow chamber; and
   a tube, wherein:
   a distal end of said tube is connected to the bottom of said hollow chamber such that the one or more weight adjusting inserts are movable within the hollow chamber by expiratory breath of a user.
2. The lung instrument training device recited in claim 1, further comprising a mouthpiece connected to a proximal end of said tube.
3. The lung instrument training device recited in claim 1, wherein one or more of said weight adjusting inserts are cylindrical.
4. The lung instrument training device recited in claim 1, further comprising a timer.

5. The lung instrument training device recited in claim 1, further comprising a metronome.

6. The lung instrument training device recited in claim 1, wherein the top and bottom of said chamber connect to a mounting plate.

7. The lung instrument training device recited in claim 1, wherein said the inner surface of said tube is lined with anti-bacterial coating.

8. A method for exercising lung capacity, comprising:
   selecting at least one weight adjusting inserts from more than one weight adjusting inserts wherein said weight adjusting inserts are selected to change the overall weight a user exercises against;
   exhaling air from a user's lung in a tube connected to a chamber;
   moving at least one of said weight adjusting inserts positioned inside said chamber; and
   regulating the position of said weight adjusting inserts within said chamber.

9. The method recited in claim 8, further comprising placing a user's mouth onto a mouthpiece connected to said tube.

10. The method recited in claim 9, wherein said tube is lined with an anti-bacterial coating containing a metal.

11. The method recited in claim 10, wherein the metal is one or more of gold, silver or copper.

* * * * *